US006436100B1

(12) United States Patent
Berger

(10) Patent No.: US 6,436,100 B1
(45) Date of Patent: Aug. 20, 2002

(54) CANNULATED INTERNALLY THREADED BONE SCREW AND REDUCTION DRIVER DEVICE

(76) Inventor: J. Lee Berger, 895 Mohawk Rd., Franklin Lakes, NJ (US) 07417

( * ) Notice: Subject to any disclaimer, the term of this patent is extended or adjusted under 35 U.S.C. 154(b) by 0 days.

(21) Appl. No.: 09/130,374

(22) Filed: Aug. 7, 1998

(51) Int. Cl.$^7$ ............................................. A61B 17/00
(52) U.S. Cl. ........................ 606/73; 606/104; 411/394
(58) Field of Search ...................... 606/78, 104, 105, 606/103, 73, 97, 98, 86, 99, 60–72; 411/394, 395, 396, 386, 116; 81/460, 436, 451

(56) References Cited

U.S. PATENT DOCUMENTS

| | | | |
|---|---|---|---|
| 1,789,060 A | | 1/1931 | Weisenbach |
| 2,121,793 A | | 6/1938 | Hanicke .................... 128/92 |
| 2,243,717 A | | 5/1941 | Moreira ..................... 128/92 |
| 2,550,866 A | * | 5/1951 | Rosan ....................... 411/359 |
| 2,823,574 A | * | 2/1958 | Rosan ....................... 411/395 |
| 4,155,162 A | * | 5/1979 | Welssman .................. 32/15 |
| 4,360,012 A | | 11/1982 | McHarrie et al. .......... 128/92 |
| 4,858,601 A | | 8/1989 | Glisson ..................... 128/92 |
| 4,878,915 A | | 11/1989 | Brantigan .................. 623/17 |
| 4,950,270 A | | 8/1990 | Bowman et al. ........... 606/72 |
| 5,129,906 A | * | 7/1992 | Ross et al. ................. 606/77 |
| 5,169,400 A | | 12/1992 | Muhling et al. ........... 606/73 |
| 5,217,462 A | | 6/1993 | Asnis et al. ............... 606/73 |
| 5,423,819 A | | 6/1995 | Small et al. ............... 606/73 |
| 5,431,651 A | | 7/1995 | Goble ....................... 606/73 |
| 5,456,267 A | | 10/1995 | Stark ........................ 128/898 |
| 5,498,265 A | | 3/1996 | Asnis et al. ............... 606/73 |
| 5,514,138 A | | 5/1996 | McCarthy .................. 606/65 |
| 5,549,677 A | * | 8/1996 | Durr et al. ................. 606/105 |
| 5,584,836 A | | 12/1996 | Ballintyn et al. .......... 606/73 |
| 5,690,633 A | | 11/1997 | Taylor et al. .............. 606/73 |

\* cited by examiner

Primary Examiner—Lee Young
Assistant Examiner—Lien Ngo
(74) Attorney, Agent, or Firm—John S. Hale; Gipple & Hale

(57) ABSTRACT

A method and apparatus for the reduction and fixation of a fractured bone, comprising the steps of drilling a plurality of bores in different bone sections of a fractured bone site and then driving bone screws having an elongated cylindrical shank with external thread and a throughgoing threaded bore running the length of said shank and a head formed at the proximal end of the shank defining an engagement structure in the form of a geometrically shaped recess which is shaped to receive torque from a driver into respective bores of different sections of a fractured bone with a driver. The driver is constructed as a cannula shaft member and has a first engagement structure formed at a distal end, a handle member mounted at the proximal end of the shaft member with a slidable rod member having a length greater than the length of the shaft member disposed within and removable from the bore of the shaft member; and a cap member secured to said proximal end of the rod member. The plurality of driving devices individually are secured to respective bone screws to form a first and a second bone fixation and reduction assembly and the first and second bone fixation assemblies are then moved toward each other transporting the sections of fractured bone to reduce the fracture with the first and second bone fixation assemblies being clamped together to effect a fixed relation between the fractured bone sections.

17 Claims, 4 Drawing Sheets

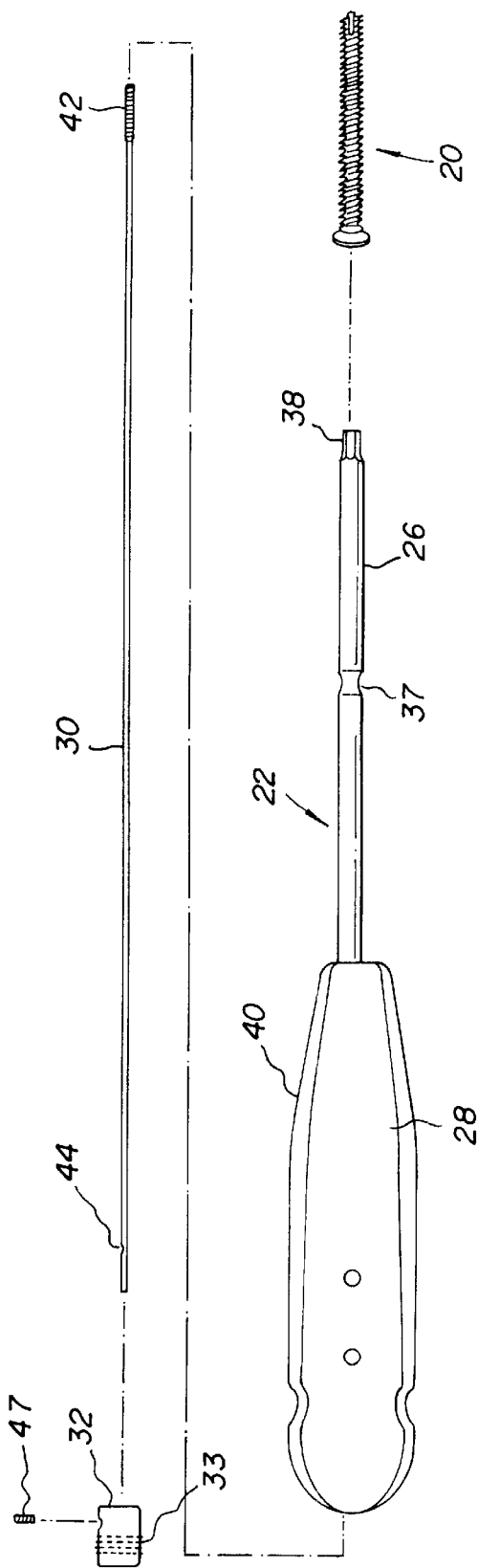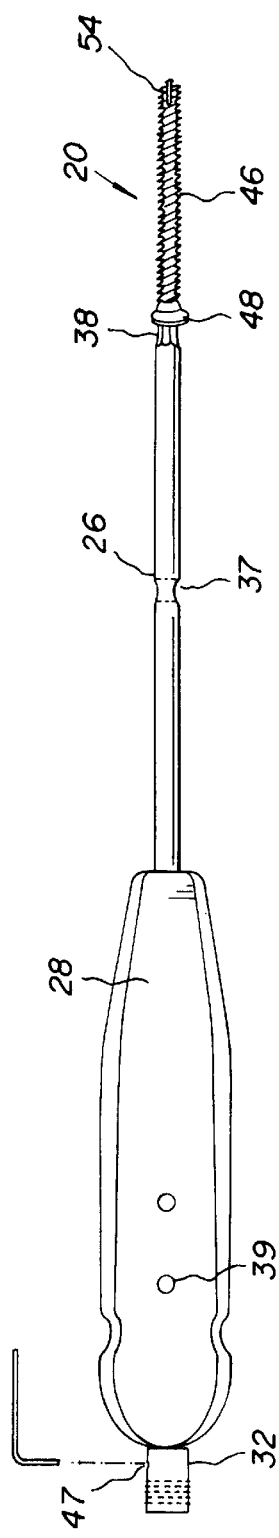
FIG. 1
FIG. 2

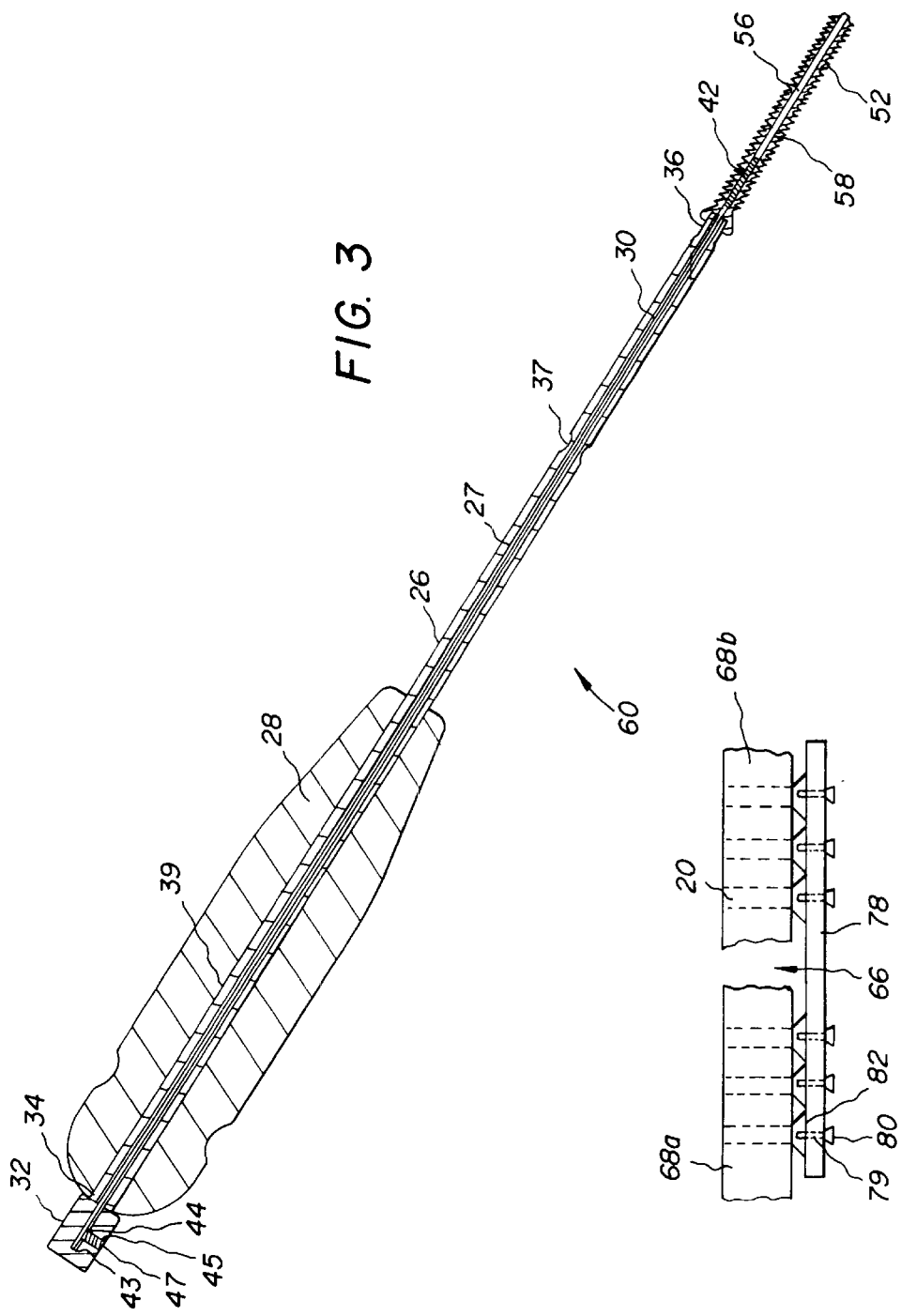
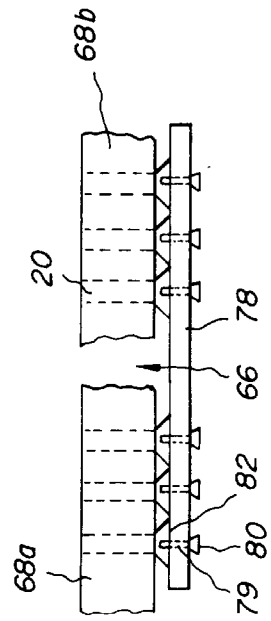

US 6,436,100 B1

CANNULATED INTERNALLY THREADED BONE SCREW AND REDUCTION DRIVER DEVICE

FIELD OF THE INVENTION

The invention generally relates to bone fracture reduction and fixation and more particularly to a cannulated, internally threaded bone screw and a reduction driving device and a method of using the same to effect the reduction and fixation of bone fractures.

BACKGROUND OF THE INVENTION

It is known to use screw-type devices and associated drivers for bone fracture repair. These screw-type devices may be used in combination with clamps to achieve bone fracture fixation. As one example of same, U.S. Pat. No. 5,498,265 issued Mar. 12, 1996 discloses a bone screw and a driver for driving the screw into a fracture site. The bone screw has a threaded shank having proximal and distal externally threaded shank portions and an internally threaded head sleeve portion which receives the threaded rod of the driver. The driver has a handle and an inner rod connected to the handle. The rod fits within the head sleeve and mates with a cutout in the proximal end of the threaded shank portion. After the screw is placed in a fractured bone, the length of the screw can be adjusted longitudinally to compress the fracture.

U.S. Pat. No. 2,243,717, issued May 27, 1941, for a surgical device shows a cannulated bone screw having a threaded end, a square shaft portion, a round shaft portion and a screw portion. A clamp formed with a head and skirt has a bore allowing it to be mounted on the threaded end. A nut is threadedly mounted on the threaded end of the bone screw. When the bone screw is used in fracture repair, the fracture site is drilled to form a bore and the screw portion of the bone screw is screwed into the bone bore using wrench members specially adapted to drive the bone screw. When the bone screw is firmly anchored in the bone, the guide wire previously inserted is withdrawn, the clamp is applied to the threaded end of the bone screw, and the nut is caused to engage the threaded end. Tightening the nut moves the clamp towards the screw portion to fix the fracture.

An example of a similar screw type device, the length of which can be adjusted to compress a fracture site can be found in U.S. Pat. No. 2,121,717 issued Jun. 2, 1930. U.S. Pat. No. 4,858,601, issued Aug. 22, 1989, is also directed toward a adjustable length screw in the form of a sectioned bone screw which is cannulated and threaded on its outer surface. The bone sections are held together by a spindle received in the cannula and soldered to a section.

Screw-type devices which are used in combination with external clamping means to achieve bone fracture reduction and fixation are also known. U.S. Pat. No. 5,690,633, issued Nov. 25, 1997, shows a fracture fixation device which combines the functions of external fixation pins and external fixation or "lag-type" screws in a single unit. The fracture fixation device includes cannulated screw means for screwing into a first bone fragment over a guide pin and engagement means in the form of a collar mounted on a rod for engaging a second bone fragment. The screw means and engagement means coact to compress first and second bone fragments. Attachment means preferably integral with the screw means has an outer end for attachment to an external fixator system which includes an elongated external fixator rod and at least a pair of external fixator connectors attached to the rod at spaced locations.

Further examples of external fixation devices and clamps can be found in U.S. Pat. No. 1,789,060, issued Jan. 13, 1931, and U.S. Pat. No. 4,360,012, issued Nov. 23, 1982.

A screw and driver for securing a bone block is disclosed in U.S. Pat. No. 5,423,819, issued Jun. 13, 1995. The screw and driver are both rotationally and axially releaseably coupled so the screw can be inserted in a downwardly facing hole. The screw is preferably threaded along its entire exterior surface length and has a blind bore which opens on the proximal end of the screw. A driver with an elongated shaft is inserted into a counterbore portion of the axial blind bore of the screw so that the front portion will compress radially. When the front portion is fully inserted, it snugly engages the wall of the bore with a minor spring biased interference so that the driver is releasably coupled to the screw. The driver also includes an elongate intermediate portion having a hexagonal cross-section and the counterbore of the screw is provided with a complimentary hexagonal cross-sectional configuration so that rotation of the intermediate portion causes rotation of the screw. In one embodiment of the screw and driver, a throughgoing axially aligned bore is provided in both the screw and the driver to accommodate a K-wire allowing the screw to slide freely along the wire.

U.S. Pat. No. 5,431,651, issued Jul. 11, 1995, shows a cross pin and set screw femoral and tibial fixation apparatus and method for mounting a ligament graft. The patent is directed towards an arthroscopic surgical procedure for replacement of a cruciate ligament in a knee and requires fixation of the ends of a ligament in a prepared tunnel. Transverse holes are drilled in the femoral tunnel during the procedure preferably using a drill guide. The apparatus includes a drill guide for drilling the transverse hole or holes which is arranged to be releasable from a first twist drill so that the first twist drill is left in place to be used for guiding further drilling and for passage of a fastener device. A K-wire or the first twist drill that has been left in place is then used for guiding a second twist drill for enlarging the transverse hole and for guiding a cannulated screw fastener device in the femoral bone end of a ligament graft that has been fitted in to the femoral tunnel section. A set screw is mounted on a forward end of a turning tool and the turning tool and set screw are cannulated to receive a K-wire. A coupling end of the turning tool is seated in a rear end recess in the set screw to mount the screw on the turning tool so that the turning tool and set screw are rotatably coupled but not axially coupled.

A cannulated bone screw is shown in U.S. Pat. No. 4,950,270, issued Aug. 21, 1990. The bone screw has an axial cannula suitable for use with a guide pin for positioning the screw in a bore. The screw is provided with an exterior screw thread having a normal helical winding for screwing insertion of the screw into a bone material. The external threading extends the length of the screw to facilitate the complete insertion of the same in the bone.

A cannulated screw and driver used in bone marrow harvesting and bone biopsy systems is shown in U.S. Pat. No. 5,456,267, issued Oct. 10, 1995. The cannulated screw has a torque receiving head and threaded shaft exterior with one embodiment including inner threads which terminate a hexagonal shaped interior portion. The head is provided with a hexagonal shaped interior portion to permit engagement with a driving tool. The screw includes a structure on one end permitting attachment of a fitting for applying negative pressure to facilitate marrow harvesting. The embodiment includes inner threads on a first end, or in the alternative, pressure fittings or twist lock fittings may be provided. The threads or other structures must provide sufficient seal to permit the negative pressure required for harvesting.

An examination of the prior art indicates the need for a fracture reduction bone screw that provides an attachment site for a bone screw driving device so that the bone screw and driving device cooperate to form an assembly which can be manually manipulated to effect fracture reduction and provide structural support for conventional clamping devices to effect bone fracture fixation.

SUMMARY OF THE INVENTION

The present invention discloses and describes a cannulated, externally and internally threaded bone screw and a driving device for same for use in the reduction and fixation of bone fractures. The head of the screw is shaped to conform to the end portion of the driving device and may be of various shapes and sizes.

The internal threading allows the bone screw to be used in a wide range of orthopedic applications. For example, the internal threading can serve as an attachment site for the driving device or may be used for fixation of orthopedic equipment such as bone plates, rods or other types of screws.

In the driving device, a distally threaded rod member and a releasable lockable cap member are used to secure an internally threaded bone screw to the distal end of the cannulated bone screw driving device. After the bone screw is driven into a bone, a bone fixation and reduction unit can be constructed by securing the bone screw to the driver device by threading an end of the rod member with the internal threading of the bone screw and rotating the cap member mounted on the proximal end of the rod member to tighten the engagement.

Because the screw is secured to the driver device by a threaded rod and because the bone screw is constructed of high grade surgical steel with machined external and internal threading, considerable force can be applied to the unit to align the bone, reduce the bone fracture and apply traction to the fracture site. The driver can be quickly detached from the screw by manually rotating the cap member to disengage the rod from the internal screw threading. This allows the bone screw and driving device to be used in a wide range of orthopedic applications. The bone screw and driving device can also be used in various ways with conventional bone plates.

The reduction and fixation assembly can be used alone or with other assemblies to align and reduce fractures. The assemblies may, for example, be secured to fractured bone sections in pairs with one assembly on each side of the fracture site, and manually manipulated to reduce the fracture. Following fracture reduction, the driving devices can be easily removed by manually manipulating the cap member, leaving the bone screw in place or the assemblies themselves may be used as external fracture fixation devices. For example, once the fracture is reduced, a handle portion of the driving device may be removed and conventional cross bars or other clamping devices may be attached between shaft portions of the assemblies to convert the assemblies into an external fixator device to effect fracture fixation.

In a first example of the use of a bone plate with the bone screw and driving device, a plurality of bone screws are driven with a first driving device into a fractured bone through the apertures in a bone plate. A plurality of driving devices are secured to bone screws on opposite sides of the fracture with respective threaded rods to provide reduction and fixation assemblies on each side of the fracture site to effect fracture alignment and reduction. Following fracture alignment and reduction, the bone screws can be tightened to hold the plate in place for fracture fixation and the driving devices are removed leaving the bone screws in the bone.

In a second example using a bone plate with the bone screw and driving device, a plurality of bone screws can be driven with a driving device into a fractured bone in alignment to receive the apertures in a bone plate and support the same. After fracture reduction with a pair of reduction and fixation assemblies, a conventional bone plate can be applied to the fracture site by mounting the plate on the aligned internally threaded bone screws with a second set of conventional screws which extend through the apertures in the bone plate and threadedly engage the internal threading of the bone screws. The head portions of the bone screws can thus be used to support a conventional bone plate or other conventional orthopedic equipment and the internally threaded cannula of each screw can receive and threadedly engage a conventional second screw to secure the bone plate or other structure to the fracture site.

Yet another object of the invention is to provide a bone screw-driver assembly of simple construction which can be used to apply traction to the fracture site.

It is an object of the invention to provide a self-drilling, self-tapping cannulated bone screw that is both externally and internally threaded. The internal threading can advantageously provide an attachment site for a reduction screw driving device that can be used to drive the internally threaded bone screws into bony tissue including cortical or cancellous bone during orthopedic surgical procedures.

It is a further object of the present invention to provide an internally threaded bone screw that can be used for bone reduction and fixation of fractured bones, for the fixation of orthopedic equipment such as plates, rods to bone, particularly fractured bone, or for the fixation of other types of screws in orthopedic procedures.

It is a further object of the invention to provide a rod member that is threaded at a distal end and cap member that is releaseably locked to a proximal end of the rod member to provide torque to the rod member.

It is also an object of the invention use the rod member and cap member to adapt a cannulated screwdriver, and a cannulated, internally threaded bone screw to construct a bone fixation and reduction assembly.

Another object of this invention is to use the bone screw driver assembly to align and reduce fractures.

Yet another object of this invention is to describe a plurality of methods for using the bone screw-driver assembly during surgical procedures following fracture alignment and reduction to effect bone fracture fixation.

It is a further object of this invention to show how a plurality of the assemblies can be used for fixation of fractures using external support structures; and to show how a driving device can be easily removed from an assembly once the bone screw is in place and the screw can be used for the application of a surgical plate to the fracture site.

These and other objects, advantages, and novel features of the present invention will become apparent when considered with the teaching contained in the detailed disclosure along with the accompanying drawings.

BRIEF DESCRIPTION OF THE DRAWINGS

FIG. 1 is a partially exploded view of the bone reduction and fixation invention showing a driver and cannulated, internally and externally threaded bone screw;

FIG. 2 is a side elevational view of the bone reduction and fixation assembly of FIG. 1;

FIG. 3 is a cross-sectional view of the bone reduction and fixation assembly of FIG. 2;

FIG. 11 is a schematic side elevational view showing a plurality of aligned internally threaded bone screws of the present invention supporting a conventional bone plate with a plurality of conventional surgical screws threadedly engaged with the threaded bone screws to secure the bone plate to the fracture site.

DETAILED DESCRIPTION OF THE PREFERRED EMBODIMENT OF THE INVENTION

Figure 4:
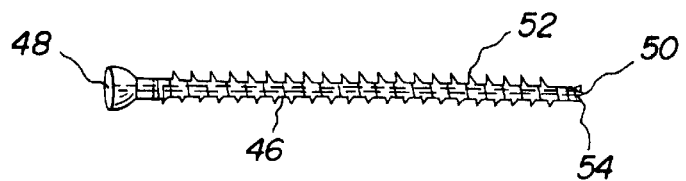
FIG. 4 is a side elevational view of a fully externally threaded cannulated and internally threaded bone screw used in the invention.

The preferred mode and best embodiment of the present invention is shown in FIGS. 1 to 7. Referring now to the drawings, FIGS. 1–3 show a cannulated, internally and externally threaded bone screw 20 and a cannulated driver device 22 constructed according to the principles of the present invention.

The driver device 22 includes a shaft member 26 defining a throughgoing bore 27, a handle 28 and includes a rod 30 and a cap member 32. The rod 30 and cap member 32 are used to releasably secure the bone screw 20 to the driver device 22 as will later be described. The shaft member 26 is an elongated, generally cylindrical structure which has a cylindrical throughgoing bore or cannula 27 best seen in the cross-sectional view of FIG. 3 which extends longitudinally from a proximal end 34 of the shaft member 26 to a distal end 36.

The shaft member 26 is an integral tubular structure preferably constructed of surgical steel, although any suitable material can be used, and includes a shaped engagement structure 38 integrally formed at the distal end 36 and one or more annular grooves 37 spaced along its length. The engagement structure 38 which preferably has a hexagonal configuration facilitates the mating and rotational engagement of the bone screw 20 with the driver as will be described and the grooves 37 may be used as attachment sites for conventional clamp members during a bone fixation procedure. It will be appreciated that the engagement structure 38 may take any angular configuration such as square, octagonal or the like and can alternatively engage the outer periphery of the screw head.

The handle 28 has a throughgoing bore 39 to receive the proximal end 34 of the shaft member 26 and is preferably constructed of wood or plastic. The handle 28 is secured to the shaft member 26 by securing the handle sections together with conventional rivets 39 or by other suitable means. The rivets do not extend into or through the bore of the shaft member 26. Alternatively, the handle member 28 may be removably mounted to the shaft member 26.

The rod 30 is an integral, solid, generally cylindrical structure preferably constructed of surgical or high grade steel and is provided with a threaded section 42 at its distal end and a machined recess or well 44 near its proximal end which receives set screw 47. The cap member 32 is a generally cylindrical structure that has a blind bore 43 to receive the proximal end of the rod 30 and a cylindrical, internally threaded passage 45 which extends from a side surface of the cap member 32 into the blind bore 43 to permit the passage of a conventional set screw 47 having an Allen head. A conical end portion of the Allen set screw is received within the well 44 in the rod 30 to lock the cap member 32 to the rod 30. The outer surface of cap 32 is knurled at 33 to allow the cap 32 and secured rod 30 to be rotated within bore 27 of the shaft 26 so that threaded end 42 can be screwed into the inner thread 58 of the cannulated bone screw 20.

The outer diameter of the cylindrical rod 30 is less than the inner diameter of the cylindrical bore 27 in the shaft member 26 so that the rod 30 can be easily received therein and pass therethrough. Conversely the threaded end section 42 has threads with an outer diameter greater than the outer diameter of bore 27 so that rod 30 cannot be pulled through the bore 27 of the shaft 26. When the cap member 32 is releaseably locked to the proximal end of the rod 30, cap member 32 prevents a portion of the proximal end of the rod 30 from entering the cannula 27 of the shaft member 26. As best seen in FIG. 3, the rod 30 is longer than the shaft member 26 so that when the cap member 32 is mounted on the rod 30 and the rod 30 is disposed within the cannula or bore 27 of the shaft member 26, the threaded section 42 of the rod 30 extends a predetermined length beyond the distal end 36 of the shaft member 26 to threadedly engage the internal threading 58 of the bone screw 20.

Figure 6:
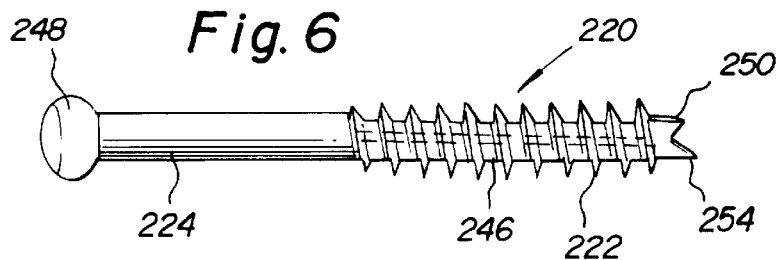
FIG. 6 is a side elevational view of a partially externally threaded, cannulated and internally threaded bone screw used in the invention.

The cannulated, internally threaded bone screw 20 shown in cross-section in FIG. 3 is mounted on the driver device 22 and is also shown in FIGS. 4 and 6. The bone screw 20 is an integral structure preferably made of surgical steel and includes a shank 46, a head 48 and a tip portion 50. The shank 46 of the bone screw 20 has an external thread 52 which is helically formed thereabout, and extends from the head 48 to the tip portion 50. The head 48 has a generally larger outer diameter than the shank 46 and defines a hexagonal shaped recess 49 so that the bone screw can receive torque from the engagement structure 38 and apply a compressive force to a bone surface or to retain a bone plate against a bone for fracture fixation. The exterior surface of the tip portion is tapered and provided with a plurality of flutes 54 so that the bone screw is self drilling. The plurality of flutes 54 extend proximally longitudinally from the tip portion 50 and may extend into the shank 46.

Figure 5:
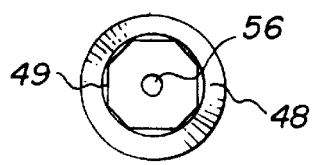
FIG. 5 is an enlarged front elevational view of the head of the bone screw of FIG. 4.

A throughgoing internal bore or cannula 56 extends from the head 48 through the shank 46 to the tip portion 50 and is provided with an internal thread 58, preferably throughout its length. As best seen in FIG. 5, a recess 49 shaped to receive the shaft engagement head 38 is formed in the head 48 of the bone screw 20. This recess is axially aligned with the cannula 56. The walls of the recess 49 have a hexagonal cross-section and define an engagement recess portion of the bone screw 20. As shown in FIG. 1, the engagement structure 38 of the driver device 22 is formed by a hexagonal configuration on the distal end of the shaft 26 and is dimensioned to be received within the recess 49 formed in the head of the bone screw 20 to rotatably engage the bone screw and the driver. It is understood that this structure is exemplary only and that the engagement portion of the bone screw may also be formed on the outer periphery of the head portion.

Figure 7:
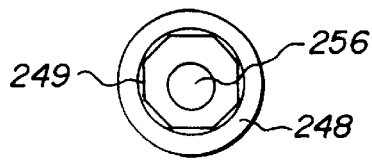
FIG. 7 is an enlarged front elevational view of the head of the bone screw of FIG. 6.

The method of bone fixation and reduction of the present invention can be performed using a wide range of cannulated, internally threaded bone screws. An alternative embodiment of an internally threaded bone screw 220 is shown in FIGS. 6 and 7. This embodiment is constructed for use in cancellous bone. The external surface of body portion 246 of the bone screw 220 is partially threaded at section 222 and smooth surfaced or unthreaded at section 224 and the tip portion 250 is provided with a plurality of flutes 254. The integral head 248 has a larger exterior diameter than the body portion and defines a hexagonal recess 249 which seats the shaft engagement end 38 and the internal threading preferably extends the entire length of the bone screw cannula 256.

The internal and exterior threads of the bone screws 20 and 220 are preferably formed by machining and the internal thread structures may partially or fully cover the wall of the respective interior bores of the bone screws 20, 220. Each the bone screws 20 and 220 is self-drilling and self-tapping.

The bone screw 20 and driver device 22 can be assembled using the rod 30 and cap member 32 as shown, for example, in FIGS. 1–3, to form a bone reduction and fixation assembly 60 which can be used to effect bone fraction reduction and fixation.

The engagement structure 38 of the shaft member 26 and the engagement seat 49 of the bone screw 20 are of complimentary size and shape so that the engagement structure 38 can be snugly received within the engagement seat 49 of the bone screw 20 to rotationally lock the driver device 22 with the bone screw 20. When the driver device 22 and bone screw 20 are so engaged, the throughgoing bore 27 of the shaft member 26 is axially aligned with the internally threaded bore 56 of the bone screw 20. The rod 30 is used to releasably axially secure the bone screw 20 to the driver device 22 by securing the cap member 32 on the rod 30 by tightening the Allen set screw 47 into the recess 44 of the rod member. The threaded section 42 of the rod 30 is threaded on the internal thread 58 projecting from the internal bore 56 of the bone screw 20 and the rod 30 is rotated by manually manipulating the cap member 32 until the bone screw 20 is tightly axially releaseably interlocked to the driver device 22. Reverse rotation will of course unlock the driver device 22 and bone screw 20.

This configuration is best seen in FIGS. 2 and 3. When thus rotationally and axially releasably interlocked, the driver device 22 and the bone screw 20 form a single assembly which is referred to as the bone reduction and fixation assembly and is generally designated by the reference numeral 60 as shown in FIG. 3. Because the bone screw 20 and driver device 22 are tightly held together by the steel rod 30, the assembly 60 does more than maintain the bone screw in engagement with the driver to facilitate screw positioning and the driving insertion thereof into cortical or cancerous bone. This rigid engagement allows the surgeon to manually manipulate the fractured bones to reduce the fracture after the screw (or screws) has been inserted (See FIG. 8) and permits fracture fixation after the fracture has been reduced through conventional bone clamps mounted between adjacent assemblies 60.

Figure 8:
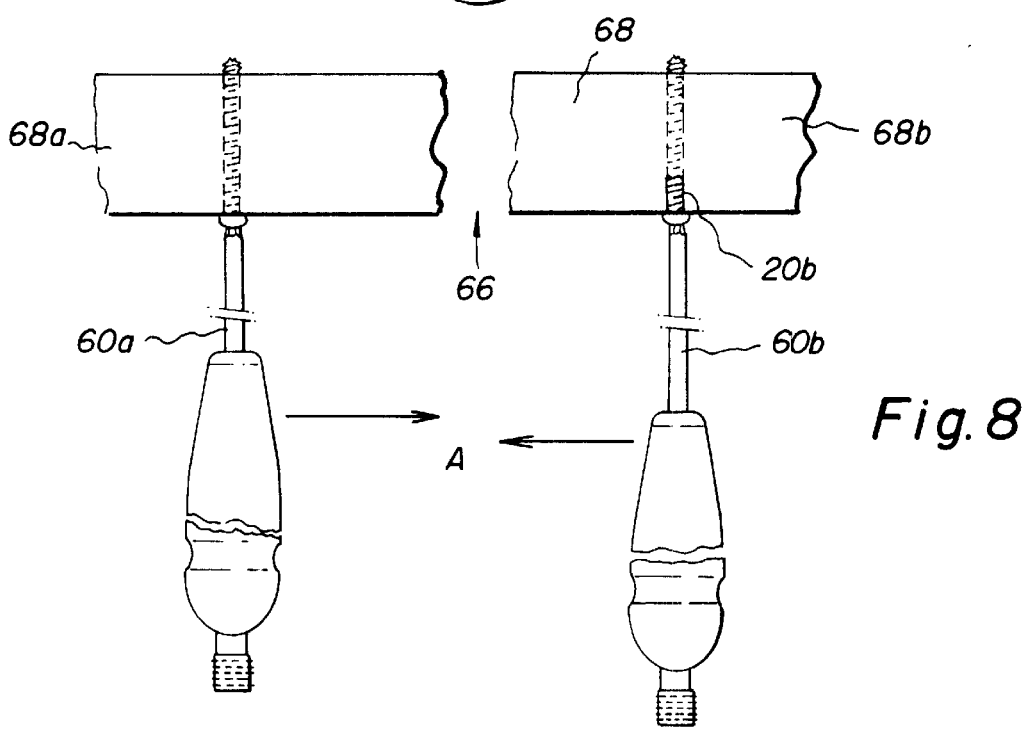
FIG. 8 is a schematic fragmentary side elevational view of a fracture site showing a plurality of bone reduction and fixation assemblies secured to portions of the fractured bone to reduce the bone fracture.

FIG. 8 shows an example of how an internally threaded bone screw can be used as a fracture reduction device at a fracture site 66 in a bone 68. In this example the fracture 66 has separated the bone 68 into two portions 68a and 68b. Two identical bone fracture reduction and fixation assemblies 60a and 60b are secured to the bone portions 68a and 68b, respectively, adjacent the fracture site 66. The description for insertion of a bone screw 20a, 20b is given with reference to assembly 60a; it being understood that bone screw 60b is inserted in the same way.

A guide hole (not shown) is formed in the cortical portion of the bone fragment 68a proximate the fracture site 66. A smooth surgical guide wire or K-wire is inserted in the guide hole. A conventional cannulated surgical drill, optionally used in conjunction with a conventional drill guide, may be used to form a guide hole. The conventional surgical guide wire or K-wire may be inserted in the guide hole through the cannula of the drill before the same is removed therefrom, leaving the guide wire in place.

With the smooth guide wire in place within the guide hole, the cannulated, internally threaded bone screw 20 is inserted over the guide wire with the cannulated driver device 22 to engage two cortices of bone. The threaded rod 30 and the cap member 32 have not been mounted on the cannulated driving device when the guide wire is used to guide the bone screw and driver to the guide hole. After the bone screw 20 is driven into the bone using the driver device 22 the smooth guide wire is removed leaving the bone screw in the bone portion 68a. The engagement end 38 of the driver device 22 is interengaged with the recess or seat 49 of the bone screw 20 and the externally threaded rod 30 is rotated and tightened into the internal thread of the cannulated screw by manually rotating the cap member 32.

The bone screw 20 and driver device 22 are thus locked together to form the bone reduction and fixation assembly 60a. As shown in FIG. 8, a second assembly 60b can be secured to the bone portion 68b using a second internally threaded bone screw 20b by repeating this procedure. The surgeon can then manipulate the bone portions 68a, 68b by grasping the handle members 28a, 28b and pulling each of the handles towards each other in direction "A" to reduce the fracture 66 manually.

Figure 9:
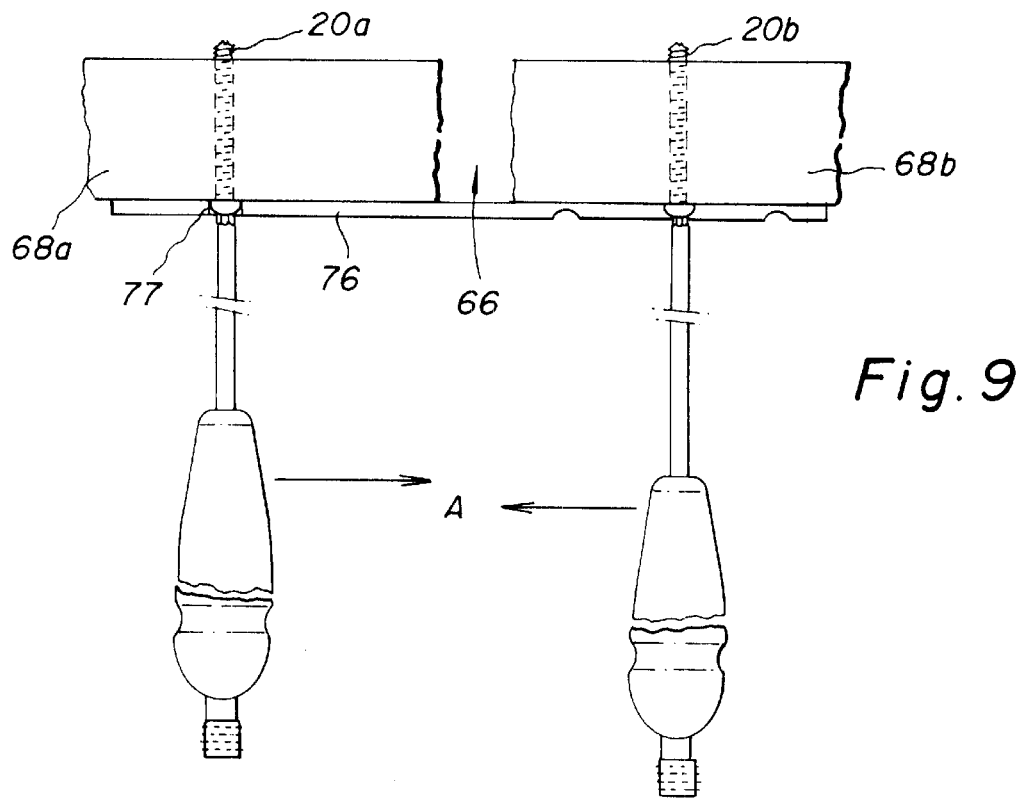
FIG. 9 is a schematic side elevational view similar to FIG. 8 showing a conventional bone plate mounted on the bone fracture sections by a plurality of reduction and fixation assemblies to effect fracture fixation.

FIG. 9 shows that the internally threaded bone reduction screw can be applied through a conventional bone fixation plate 76 which is shown in place over the fracture site 66. When the cannulated, internally threaded bone screw 20 is used with a conventional fixation plate 76, typically at least one of the bone screws 20a or 20b is inserted through an elongated slot 77 in the plate so that the bone portions 68a and 68b can be brought together in direction "A" to reduce the fracture 66 before the plate 76 is firmly fastened on the bone portions.

Figure 10:
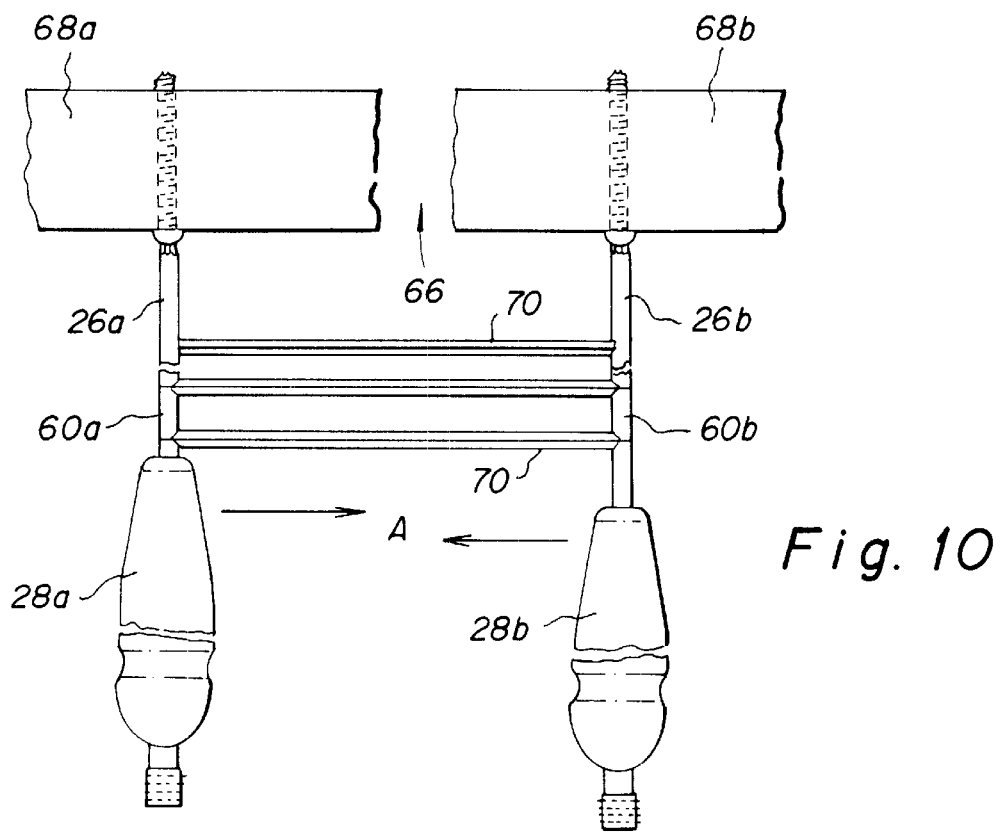
FIG. 10 is a schematic side elevational view similar to FIG. 8 showing a plurality of conventional clamping devices mounted on the bone reduction and fixation assemblies to effect fracture fixation.

FIG. 10 shows that when the bone fracture 66 has been appropriately aligned and reduced by the assemblies 60a, 60b, conventional external fixator cross bars 70 can be mounted between the shaft members 26a, 26b so that the assemblies 60a, 60b can be used for bone fixation holding bone segments 68a, 68b in a fixed position. Although the handles 28a, 28b are shown still in place on the assemblies 60a, 60b and have previously been described as being mounted to the shaft member 26 with conventional rivets, it is within the scope of the invention to provide a removable handle 28 on each assembly 60 so that the handles can be removed after the external fixator cross bars 70 have been mounted therebetween to hold the fractured bone together.

The external fixator cross bars 70 are conventional and the structure thereof and the method of mounting the same is well known. Conventional devices such as the cross bars 70 typically are comprised of a rigid central bar structure and a conventional clamping device mounted on each end of the bar structure and are well known in the art. Any conventionally known clamping device or cross bar can be used with the assemblies 60 to form an external fixator.

The firm fixation of the inventive bone screw 20 is superior to Schantz screws or other types of external fixation pins and should result in decreased incidence of pin loosening.

The externfixation device can be easily removed in one step by loosening the bone screw 20 with the driver device 22.

FIG. 11 shows a plurality of internally threaded bone screws 20 cooperating to form a fixation site to receive and support a conventional bone plate 78. The cortical bone screws 20 are inserted in the bone portions 68a, 68b in appropriate vertical and horizontal alignment to receive a second set of conventional surgical screws 80 which extend through the slots or cylindrical apertures 79 formed in the bone plate 78. The top surfaces of the heads of the bone screws 20 form support surfaces to support the bone plate 78.

The bone plate 78 may be affixed to the bone 68 by forming a series appropriately aligned and appropriately directed guide holes in the bone portions 68a and 68b. A conventional drill and drill guide may be used for this purpose. As each guide hole is formed, a bone screw 20 is placed therein using a K-wire as previously described. Two or more reduction and fixation assemblies 60 may be used in the manner described above to manually reduce the fracture before the conventional plate is applied. When the desired number of bone screws 20 are placed in the bone fragments 68a, 68b, the bone plate 78 is placed on the heads of the bone screws which have flat or other appropriately shaped surfaces thereon to support the bone plate 78.

In the example illustrated in FIG. 11, the top surfaces 82 of the bone screws 20 are planar and the screws have been placed in the bone such that the top surfaces 82 are essentially coplanar. The bone screws 20 are aligned to coincide with the apertures in the bone plate 78. The surgical screws 80 are screwed into the internal threading of the bone screws 20 to secure the plate to the fracture site 66.

It is clear from the forgoing that the machined internal threading of the self-drilling, self-tapping cannulated screw described herein, provides the orthopedic surgeon with many ways to effect fracture reduction and fixation. The threaded rod 30 can be used with a cannulated driving device, including many conventional cannulated driving devices, to form a fracture fixation and reduction assembly 60 of the invention.

When the bone screw 20 and driver device 22 are secured together to form the assembly 60, this fixed assembly can be used as a fracture reduction tool to assist in aligning fractures of bone. The assembly 60 can also be used to apply traction to a fracture site. The screw can be inserted directly into bone or through a conventional fixation plate.

In addition to this use in internal fixation of fractures of the bone, the assembly 60 can be used as an external fixation device for bone fractures. Once the fracture is reduced, the handle of the driver device 22 may be removed and cross bars 70 may be attached to the shaft member 26 converting the assembly 60 to an external fixator device.

The internally threaded screw can be used independently as a bone fixation screw. The internal threads may be used to apply optional devices such a screws, plates or rods for other fixation purposes. It is understood that the bone screws shown herein are exemplary only and not intended to be limiting. One skilled in art will appreciate that the internally threaded cannulated screws can be manufactured in various shapes and sizes and that the internal threads may partially or fully encompass the length of the bone screws.

In the foregoing description, the invention has been described with reference to a particular preferred embodiment, although it is to be understood that specific details shown are merely illustrative, and the invention may be carried out in other ways without departing from the true spirit and scope of the following claims:

I claim:

1. A combination bone screw and driver assembly for driving a cannulated internally threaded bone screw, comprising:

a bone screw with an elongated cylindrical shank having a proximal end, a distal end, an outer surface; a head integrally formed at the proximal end and a tip portion formed at the distal end; a cylindrical throughgoing bore extending through said head and shank; an engagement structure formed in said head shaped to engage and receive torque from a driver having an end portion with a shape complimentary to the shape of the engagement structure; an external thread formed on said shank outer surface running at least one half the length of the shank outer surface and an internal thread formed on a surface defining said inner cylindrical bore running substantially the length of the shank;

said driver comprising a shaft member defining an internal throughgoing bore and an engagement structure formed at the distal end of said shaft member to engage the shaft member to a complimentary engagement structure formed in said head of the internally threaded screw to apply torque thereto;

a handle member mounted to the proximal end of said shaft member;

a rod removably mounted within said shaft member bore, said rod having a length which is greater than the length of the shaft member, and an outer diameter which is less than the inner diameter of said shaft member bore, said rod defining a thread portion formed at one end which can be threaded along the internal thread of said bone screw; and a cap member removably mounted on the other end of said rod to apply torque to said rod and retain said rod within said shaft member when said bone screw is threadedly engaged on said one end of said rod.

2. A combination bone screw and driver assembly as claimed in claim 1 wherein said handle member has two sections, each of which defines a longitudinal groove which when aligned form a bore to receive the proximal end of said shaft member.

3. A combination bone screw and driver assembly as claimed in claim 1 wherein said handle member has a unitary body which defines a longitudinal bore allowing the the proximal end of said shaft member to be mounted therein.

4. A combination bone screw and driver assembly as claimed in claim 1 wherein said rod thread portion has a greater diameter than the shaft member cannula.

5. A combination bone screw and driver assembly as claimed in claim 1 wherein said shaft member defines at least one annular groove along its length.

6. A combination bone screw and driver assembly as claimed in claim 1 further comprising a release member mounted in said cap member, said release member being movable between a released position and a locked position so that the cap member is selectively rigidly secured to said rod member when the release member is in the locked position and removable from said rod member when the release member is in the released position.

7. A combination bone screw and driver assembly as claimed in claim 1 wherein said release member is a set screw with a Allen head.

8. A combination bone screw and driver assembly as claimed in claim 1 wherein said cap member is cylindrical and knurled on the outside surface.

9. A combination bone screw and driver assembly as claimed in claim 6 wherein said rod includes a well formed at the proximal end thereof which well cooperates with said release member to releaseably lock the cap member to the rod.

10. A combination bone screw and driver assembly for driving a cannulated internally threaded bone screw, comprising:

a bone screw with an elongated cylindrical shank having a proximal end, a distal end, an outer surface with an external thread formed thereon; a head integrally formed at the proximal end and a tip portion formed at the distal end; a cannula extending through said head and shank defining an inner throughgoing cylindrical bore running along the longitudinal axis of said bone screw; an engagement structure formed in said head shaped to receive torque from a driver having an engagement structure with a shape complimentary to the shape of the engagement structure; and an internal thread formed on a surface defining said inner throughgoing cylindrical bore running along the length of said cylindrical bore;

said driver comprising a shaft member defining an internal throughgoing cannula and an engagement structure formed at the distal end of said shaft member to engage the shaft member to a complimentary engagement structure formed on the head of said cannulated internally threaded screw; said shaft member additionally defining at least one annular groove along its outer surface;

a handle member removably mounted to the proximal end of said shaft member;

a cylindrical rod movably disposed within said shaft member cannula, said cylindrical rod having a length which is greater than the length of the shaft member and a section with an outer diameter which is less than the diameter of said shaft member cannula, said cylindrical rod defining a thread portion formed at one end having a thread outer diameter which is greater than the diameter of said shaft member cannula extending beyond an end of said shaft and which can be threaded along the internal thread of said bone screw; and a cap member removably mounted on the other end of said cylindrical rod to retain said cylindrical rod within said shaft member when a bone screw is threadably engaged with the thread portion of said cylindrical rod.

11. A method for the reduction and fixation of a fractured bone, comprising the steps of:

a) drilling a plurality of bores in different bone sections of a fractured bone site;

b) driving bone screws into respective bores of said different sections of a fractured bone with a driver device;

said driver device comprising;

a shaft member having a throughgoing cannula and an first engagement structure formed at a distal end;

a handle member mounted at the proximal end of said shaft member; a rod member having a length greater than the length of the shaft member and slidably disposed within and removable from the cannula of the shaft member; and a cap member secured to said proximal end of said rod member;

each of said bone screws comprising;

a shank with a throughgoing cannula running along the longitudinal axis of said shank, a head portion integrally formed at the proximal end of said shank defining an engagement structure for said shaft member engagement structure and adapted to receive torque from said shaft member engagement structure;

an exterior thread formed on the exterior surface of said shank allowing said shank to be threaded into a bone;

an interior thread formed on an interior surface of said shank defining said cannula;

c) securing a plurality of driving devices individually to respective bone screws to form a first and a second bone fixation and reduction assembly;

d) moving the first and second bone fixation and reduction assemblies toward each other transporting the sections of fractured bone to reduce the fracture; and e) clamping the first and second bone fixation and reduction assemblies together to effect a fixed relation between the fractured bone sections.

12. A method for the reduction and fixation of a fractured bone as claimed in claim 11 including the steps of:

guiding a bone screw and an associated driving device with the rod member removed into a first guide hole in a bone portion of the fractured bone with a guide wire;

removing the guide wire from the first bone screw and from the first driving device; and placing a rod of the first driving device into the cannula thereof and rotating the cap member to secure the first driving device to the bone screw.

13. A method for the reduction and fixation of a fractured bone as claimed in claim 11 wherein the distal threaded end of each rod member threadably engages the interior thread of the associated bone screw; and the cap member is rotated to tighten the shaft member to the bone screw.

14. A method for the reduction and fixation of a fractured bone as claimed in claim 11 including a step after step a) of: placing a planar bone plate with a plurality of elongated slots over the fracture site so that the slots overlie the bores in adjacent bone sections; and replacement of step (e) with the step of securing the first and second bone fixation assemblies in the bone plate.

15. A method for the reduction and fixation of a fractured bone with a bone plate comprising the steps of:

assembling a plurality of screw driving assemblies, a bone plate, a plurality of bone screws, a plurality of secondary screw members and a guide wire, each driving device comprising;

a shaft member defining a cannula from the proximal end to the distal end and an engagement structure at the distal end;

a handle member removably mounted at the proximal end of said shaft member;

a rod member mounted within the cannula of said shaft member, said rod member being provided with a threaded portion at the distal end; and a rotatable cap member releaseably secured to said proximal end;

each bone screw comprising;

a shaft body with an integral head and a throughgoing cannula formed in said body running from the head to the distal end;

an external thread formed on an exterior surface of said body covering at least one half the length of said body and an interior thread formed on an interior surface defining said cannula running substantially the length of said cannula; and an engagement structure formed on said head;

said bone plate comprising;

an essentially planar base member with a plurality of elongated slots formed therein;

placing the bone plate adjacent the fracture site with the slots positioned over bores drilled in bone sections of said fracture site;

guiding a bone screw through a first slot on the bone plate into a bore and driving the first bone screw into a first section of a fractured bone;

guiding a second bone screw through a second slot on the bone plate into another bore and driving the second bone screw into a second section of a fractured bone;

securing a first and a second bone screw-driving device assembly to the first and second bone screws, respectively;

applying force to the first and second bone screw-driving device assemblies to reduce the distance between fracture sections; and securing the screw driving device assemblies together to effect the fixation of the fracture site.

16. The method of claim 15 for the repair of a fractured bone further comprising the step of clamping said first bone screw driving assembly to said second bone screw driving assembly to effect fixation of the fracture site.

17. The method of claim 15 for the repair of a fractured bone wherein each bone reduction and fixation assembly is provided with a removable handle and wherein the method further comprises the step of:

connecting a plurality of rods to said first bone screw driving assembly and said second bone screw driving assembly to effect fixation of the fracture site.

* * * * *